(12) United States Patent
McKee

(10) Patent No.: US 10,908,140 B2
(45) Date of Patent: Feb. 2, 2021

(54) INTEGRATED USER INTERFACE FOR STATUS AND CONTROL OF A SUBMERSIBLE MULTI-PARAMETER SONDE

(71) Applicant: In-Situ, Inc., Ft. Collins, CO (US)

(72) Inventor: Duane B. McKee, Ft. Collins, CO (US)

(73) Assignee: IN-SITU, INC., Fort Collins, CO (US)

( * ) Notice: Subject to any disclaimer, the term of this patent is extended or adjusted under 35 U.S.C. 154(b) by 0 days.

(21) Appl. No.: 16/546,124

(22) Filed: Aug. 20, 2019

(65) Prior Publication Data

US 2019/0369077 A1     Dec. 5, 2019

Related U.S. Application Data

(62) Division of application No. 14/937,152, filed on Nov. 10, 2015, now Pat. No. 10,429,369.

(60) Provisional application No. 62/077,627, filed on Nov. 10, 2014, provisional application No. 62/077,528, filed on Nov. 10, 2014.

(51) Int. Cl.
*G01N 33/18* (2006.01)

(52) U.S. Cl.
CPC ................. *G01N 33/1886* (2013.01)

(58) Field of Classification Search
None
See application file for complete search history.

(56) References Cited

U.S. PATENT DOCUMENTS

| | | |
|---|---|---|
| 5,099,920 A | 3/1992 | Warburton et al. |
| 5,259,452 A | 11/1993 | Wittrisch |
| D371,517 S | 7/1996 | Narayanan |
| 5,596,193 A | 1/1997 | Chutjian et al. |
| 5,820,416 A | 10/1998 | Carmichael |
| D418,073 S | 12/1999 | Kreutzer et al. |
| 6,157,029 A | 12/2000 | Chutjian et al. |
| 6,305,944 B1 | 10/2001 | Henry et al. |

(Continued)

FOREIGN PATENT DOCUMENTS

| | | | |
|---|---|---|---|
| CN | 102495420 | * 6/2013 | ......... G01N 33/1886 |
| EP | 1851537 | 9/2013 | |

(Continued)

OTHER PUBLICATIONS

Gurkan Tuna, Continuous Monitoring of Water Quality Using Portable and Low-Cost Approaches, May 13, 2013, 11 pages. (Year: 2013).*

(Continued)

*Primary Examiner* — Tung S Lau
(74) *Attorney, Agent, or Firm* — Leydig, Voit & Mayer, Ltd.

(57) ABSTRACT

Provided are multi-parameter sonde systems having a unique integrated user interface for ease of set-up and control, service and maintenance, even in the field and without accessory controllers. The necessary components, such as central processing unit, display and accelerometer are positioned in a water-tight housing, with the display configured for convenient observability and readability. A plurality of sensors provide electronic signals to the CPU, such as by a measurement subsystem. Upon a controlled change in orientation or a force application to the sonde, the display via the accelerometer provides a desired output display configuration.

14 Claims, 9 Drawing Sheets

(56) References Cited

U.S. PATENT DOCUMENTS

| | | |
|---|---|---|
| 6,677,861 B1 | 1/2004 | Henry et al. |
| 6,779,383 B2 | 8/2004 | Lizotte et al. |
| 6,798,347 B2 | 9/2004 | Henry et al. |
| 6,928,864 B1 | 8/2005 | Henry et al. |
| 6,938,506 B2 | 9/2005 | Henry et al. |
| 6,943,686 B2 | 9/2005 | Allen |
| 7,007,541 B2 | 3/2006 | Henry et al. |
| 7,138,926 B2 | 11/2006 | Henry et al. |
| 7,142,299 B2 | 11/2006 | Tokhtuev et al. |
| 7,470,917 B1 | 12/2008 | Hoang et al. |
| D616,314 S | 5/2010 | Akomolede |
| 7,832,295 B2 | 11/2010 | Rodriguez et al. |
| 7,900,528 B2 | 3/2011 | Vincent |
| 8,429,952 B1 | 4/2013 | Bringhurst et al. |
| 8,488,122 B2 | 7/2013 | Dong et al. |
| 8,514,066 B2 | 8/2013 | Harmon |
| 8,542,189 B2 | 9/2013 | Milne et al. |
| 8,555,482 B2 | 10/2013 | Metzger |
| 8,797,523 B2 | 8/2014 | Clark |
| 9,292,191 B2 | 3/2016 | Kim et al. |
| D755,655 S | 5/2016 | Scott et al. |
| D787,962 S | 5/2017 | Scott et al. |
| D787,963 S | 5/2017 | Scott et al. |
| D787,964 S | 5/2017 | Scott et al. |
| 9,689,855 B2 | 6/2017 | Scott et al. |
| 9,778,180 B2 | 10/2017 | Baltz et al. |
| D803,081 S | 11/2017 | Scott et al. |
| 9,835,554 B2 | 12/2017 | Scott et al. |
| 10,302,616 B2 | 5/2019 | Scott et al. |
| 10,365,097 B2 | 7/2019 | Steinbach et al. |
| 10,393,654 B2 | 8/2019 | Baltz et al. |
| 10,429,369 B2 | 10/2019 | McKee et al. |
| 2003/0117623 A1 | 6/2003 | Tokhtuev et al. |
| 2007/0140921 A1 | 6/2007 | Mitchell |
| 2009/0158819 A1 | 6/2009 | Vincent |
| 2010/0321046 A1 | 12/2010 | Randall et al. |
| 2011/0023586 A1 | 2/2011 | Leyer et al. |
| 2011/0273710 A1 | 11/2011 | Dong et al. |
| 2012/0242993 A1 | 9/2012 | Schick et al. |
| 2012/0262618 A1 | 10/2012 | Weakly |
| 2013/0090789 A1 | 4/2013 | DeDonato |
| 2013/0217979 A1 | 8/2013 | Blackadar et al. |
| 2014/0017143 A1* | 1/2014 | Clark .................... G01N 21/78 422/402 |
| 2016/0146777 A1* | 5/2016 | McKee ............. G01N 33/1886 702/50 |
| 2017/0176183 A1* | 6/2017 | Steinbach ............. G01B 21/18 |
| 2017/0316366 A1 | 11/2017 | Haddy et al. |
| 2018/0166772 A1 | 6/2018 | Wei et al. |
| 2018/0202929 A1 | 7/2018 | Scott et al. |
| 2019/0310236 A1 | 10/2019 | Scott et al. |
| 2019/0392212 A1* | 12/2019 | Sawhney ........... G06K 9/00201 |
| 2020/0064261 A1 | 2/2020 | Baltz et al. |

FOREIGN PATENT DOCUMENTS

| | | | |
|---|---|---|---|
| WO | WO 2006/088829 | | 8/2006 |
| WO | WO 2011/109740 | | 9/2011 |
| WO | WO 2016077322 | * | 5/2016 ......... G01N 33/1886 |

OTHER PUBLICATIONS

Mark Pedley, Tilt Sensing Using a Three-Axis Accelerometer, 22 pages (Year: 2013).*

Asanuma et al. (2001) "Miniaturized Silicon-Capacitive Accelerometer for Downhole Seismic Measurement" Proceedings of IPACK'01, The Pacific Rim/ASME International Electronic Packaging Technical Conference and Exhibition, Kauai, Hawaii, pp. 1-4.

Examiner's Report for corresponding CA Application No. 163113, dated Nov. 16, 2015, 3 pages.

Extended European Search Report, EP Application No. 15859317.8, dated May 23, 2018.

Hydrolab HL4 http://hydrolab.com/hydrolab-hl4-multiparameter-sonde/, webpage publicly available at least as early as May 6, 2014.

In Situ TROLL 9500 Multiparameter Sonde, https://in-situ.com/products/water-quality-testing-equipment/troll-9500-multiparameter-sonde/, webpage publicly available at least as early as Apr. 1, 2015.

In Situ Aqua TROLL 600 Multiparameter Sonde, https://in-situ.com/products/water-quality-testing-equipment/aqua-troll-600-multiparameter-sonde/, webpage publicly available at least as early as Sep. 14, 2015.

In Situ AquaTROLL 600 Product Information, https://in-situ.com/blog/introducing-the-aqua-troll-600-water-quality-platform-2/, webpage publicly available at least as early as Sep. 21, 2015.

In Situ AquaTROLL 600 Specification Sheet, https://in-situ.com/wp-content/uploads/2015/09/Aqua_TROLL_600_Spec.pdf, webpage publicly available at least as early as Apr. 30, 2016.

In Situ Water Quality Testing Equipment Products, https://in-situ.com/product-category/water-quality-testing-equipment/, webpage publicly available at least as early as Apr. 1, 2015.

International Search Report with Written Opinion corresponding to International Patent Application No. PCT/US2015/059925, dated Jan. 20, 2016, 8 pages.

International Search Report with Written Opinion corresponding to International Patent Application No. PCT/US2015/059920, dated Jan. 29, 2016, 7 pages.

International Search Report and Written Opinion corresponding to International Patent Application No. PCT/US2015/059918, dated Feb. 1, 2016, 8 pages.

International Search Report with Written Opinion corresponding to International Patent Application No. PCT/US2015/059939, dated Jan. 13, 2016, 9 pages.

Ott Hydrolab DS5 http://www.ott.com/products/water-quality/hydrolab-ds5-multiparameter-data-sonde/, webpage publicly available at least as early as Oct. 2014.

Sonde Wikipedia, accessed Nov. 4, 2015.

Teledyne Isco AQ700 Water Quality Multi-Parameter Sonde, 2 pages, Sep. 2013.

YSI EXO1 Multiparameter Sonde, http://www.ysi.com/productsdetail.php?EXO1-Water-Quality-Sonde-89, webpage publicly available at least as early as Oct. 2014.

YSI EXO2 Multiparameter Sonde, https://www.ysi.com/EXO2, webpage publicly available at least as early as Oct. 2014.

6-Series Multiparameter Water Quality Sondes, YSI Environmental, dated Aug. 24, 2006, 14 pages.

* cited by examiner

INTEGRATED USER INTERFACE FOR STATUS AND CONTROL OF A SUBMERSIBLE MULTI-PARAMETER SONDE

CROSS-REFERENCE TO RELATED APPLICATIONS

This application is a divisional application of U.S. application Ser. No. 14/937,152, filed Nov. 10, 2015. U.S. application Ser. No. 14/937,152 claims the benefit of priority of U.S. Provisional Application Ser. Nos. 62/077,627 and 62/077,528, each filed Nov. 10, 2014, the disclosure of each of which are incorporated herein by reference in their entireties to the extent not inconsistent herewith.

BACKGROUND OF INVENTION

Provided herein are user interfaces that are integrally connected with submersible water quality instruments containing multiple sensors for measuring a plurality of water-related parameters. The user interface facilitates user control of both the instrument and status information of the instrument.

Conventional multi-parameter sondes provide little or no status information concerning their operating state without having to connect an external accessory such as a computer or dedicated reader. Current multi-parameter sondes simply utilize one or more small light emitting diodes (LED) that may be on, off, or blinking based on the status of the sonde. The LEDs are limited in the useful information that they can convey, requiring the connection of an external accessory to obtain more important information. There is, therefore, a need for an integrated user interface that provides a user with status and diagnostic information about the state of the sonde without requiring the connection of external accessories or compromising any watertight seals.

SUMMARY OF THE INVENTION

The integrated user interfaces provided herein addresses the need in the art for status information from a submersible multi-parameter sonde. Conventional submersible multi-parameter sondes provide little or no status information concerning their operating state, without having to connect an external accessory such as a computer or dedicated reader. The integrated user interface described herein addresses those limitations to provide a user with status and diagnostic information about the state of the sonde without requiring the connection of external accessories or compromising any watertight seals. Accordingly, provided herein are submersible sondes having an integrated user interface that provides improved user control, even without external connections to controllers or displays, such as to computers, laptops, handhelds, or other separate devices. This can be of significant importance, given the location of the sondes may be in remote areas where if there is a malfunction, loss, damage, or even oversight with respect to bringing such a controller, many hours or days may be wasted. This is avoided herein as the sonde itself can be used to rapidly and efficiently set any number of desired conditions or states, particularly for sondes that may have a plurality of different sensors, each requiring individualized control.

Examples of information that the integrated user interface may provide to a user includes, but is not limited to: sonde deployment readiness; watertight status of all accessory ports; operational status of data logging functions; battery condition and external power connections; current readings of connected sensors. The integrated user interface also provides a user with control over various sonde functions including, but not limited to: configuring modes of operation; configuring data logs; starting and stopping data logs; calibrating sensors, and display control.

The user interface can be generally described as having a display module, such as a liquid crystal display (LCD) and a 3-axis digital accelerometer electronically connected to the central processing unit (CPU) of a submersible multi-parameter sonde. The user interface and related electronics, described herein as a measurement subsystem of the sonde, are housed in a clear, watertight housing. The housing may be made from a plastic and constructed to maintain a water-tight system when submerged, including when submerged up to about 1300 feet, up to about 1000 feet, up to about 650 feet, or up to a maximum submerged death that is greater than or equal to 600 feet and less than or equal to 1300 feet, or any sub-ranges thereof.

The display is visible to a user through the clear housing, permitting the sonde CPU to present status and diagnostic information to a user while maintaining the watertight integrity of the sonde.

The user can change the information presented on the display by changing the orientation of the sonde, and can control sonde functionality by tapping the sonde in response to options presented on the display. The accelerometer detects the orientation and motions of the sonde and provides this information to the sonde CPU, which in turn implements the user's selections. The accelerometer detects changes in orientation and motion from within the sonde housing and thus does not compromise the integrity of the watertight housing. The accelerometer further allows the user to actively control output display and control various aspects of the display and sonde function by a combination of sonde tapping and changes in sonde orientation.

In an embodiment, the invention is an integrated user interface for use in a submersible multi-parameter sonde. The integrated user interface comprises a water-tight housing defining a water-tight volume, wherein the water-tight housing is at least partially optically transparent. Positioned in the water-tight housing and volume is a central processing unit (CPU), a display electronically connected to the CPU, an accelerometer electronically connected to the CPU and a measurement subsystem in electronic contact with the CPU and that provides an input to the CPU from a plurality of sonde sensors. The accelerometer is configured to detect a change in orientation or an exerted force to thereby control an output display configuration of the display.

Any of the integrated user interfaces described herein may be incorporated into a sonde, including any of the sondes described in U.S. Pat. App. No. 62/077,528 titled "SUBMERSIBLE MULTI-PARAMETER SONDE HAVING A HIGH SENSOR FORM FACTOR SENSOR" filed Nov. 10, 2014, and specifically incorporated by reference herein. For example, the integrated user interface may further comprise a plurality of sonde sensors operably connected to the display for displaying a display value dependent on an output from at least one sonde sensor and in the output display configuration that is controlled by the accelerometer. The connection of the sensors may be via the measurement subsystem and the sonde CPU.

The plurality of sonde sensors is electronically connected to the measurement subsystem and the connection may pass through the water-tight housing in a water-tight configuration.

The plurality of sonde sensors may be positioned in a sensor housing, such as a sensor guard, and the integrated user interface is connected to the sensor housing with an outer-facing surface that is substantially contiguous with an outer-facing surface of the housing. In this aspect, "substantially contiguous" refers to a surface that is substantially level with another surface, such as for a cylindrical shape having a smooth cylindrical surface between the cylindrical housing and the sensor outer-facing surface. The maximum difference between outer surfaces may be described in terms of a gap or step that is independently selected to be less than 1 cm, less than 1 mm, or not observably different. As desired, other components may facilitate the connection, such as o-rings, snap fits, threaded connections, or other fastening means known in the art, and combinations thereof. As desired, the connection may be water-tight.

Any of the accelerometers described herein may be a three-axis digital accelerometer. The accelerometer may detect an orientation of the multi-parameter sonde and based on the orientation sends an electronic signal to the CPU to energize the display. Similarly, the accelerometer can detect a physical force corresponding to a tapping or double tapping force and send an electronic signal to the CPU to effect a change in the output display. The physical force may be provided to any outer surface of the sonde, or may be required to be localized to a certain area, such as a tapping on the display itself or another region having a label or other indication to a user for force exertion.

The integrated user interface provides a great flexibility as to what is displayed, based on the user's interest. For example, the output display can display to a user a status parameter; a diagnostic parameter, or a status and a diagnostic parameter. The output display may correspond to one or more of: sonde deployment readiness; watertight status of all accessory ports; operational status of data logging functions; battery condition; external power connections; or readings from connected sensors.

The accelerometer may detect a physical force corresponding to a tapping or double tapping for control of a sonde function, the sonde function comprising one or more of: operation mode configuration; data log configuration; initiating data logs; terminating data logs; or sensor calibration.

The water-tight housing may be formed from a unitary material that is optically transparent. For example, the unitary material may comprise a clear plastic housing that is cylindrically shaped. The cylindrical shape is useful in that the housing may then connect to a correspondingly cylindrically shaped sensor housing that contains a plurality of sensors. Of course, the system is compatible with individual sensors each enclosed in a separate housing, wherein the plurality of housings together form a cylindrical shape, and optionally, the housings are positioned within an inner volume of a sensor guard.

A sleeve with a viewing window may be used to further emphasize the position of the display to a user. The sleeve may circumferentially surround the water-tight housing with the viewing window aligned with the display. To ensure a tight-fit, the sleeve may be flexible with an elastically-generated contact force to maintain the sleeve in tight contact with the water-tight housing. Alternatively, the water-tight housing may comprise an optically transparent portion and a non-optically transparent portion, the optically transparent portion aligned with the display and configured to allow a user to view the display through the water-tight housing. These two different properties may be obtained by various means, such as by using a two-shot clear/color mold.

The integrated user interface may have a display comprising a liquid crystal display. The display may further comprise a back light to facilitate observations in low light conditions.

The integrated user interface may be contained in a water-tight housing or volume that is water-tight to a maximum depth that is greater than or equal to 600 feet and, optionally, less than or equal to 1300 feet.

Also provided herein are various methods related to any of the integrated user interfaces and sondes described herein. For example, the method may be for displaying status and diagnostic information of a submersible multi-parameter sonde on an outer-facing surface of the submersible multi-parameter sonde. The method may comprise the steps of exerting a force on a three-axis digital accelerometer in a submersible multi-parameter sonde; outputting to a processor a signal from the three-axis digital accelerometer based on the exerted force; processing the signal with the processor to determine a force parameter; and generating an output display on a display observable to an operator or user based on the force parameter; wherein the accelerometer, the processor and the display are contained in a water-tight housing and the output display provides sonde status, diagnostic information or status and diagnostic information.

The exerted force may correspond to shaking/vibrating the sonde, tapping or double tapping the sonde; or changing an orientation of the sonde between an upward and downward facing direction. The changing the orientation step may change a state of the sonde from a sleep mode to an active mode that provides the output display. The tapping provides user-control over a sonde function.

The output display may comprise sonde deployment readiness; watertight status of an accessory port; operational status of all data logging functions; battery condition; external power connection; and/or readings from connected sensors. The sonde function comprises user control of: operation mode; data log configuration; starting and stopping of data logs; and/or sensor calibration.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

DETAILED DESCRIPTION OF THE INVENTION

Figure 1:
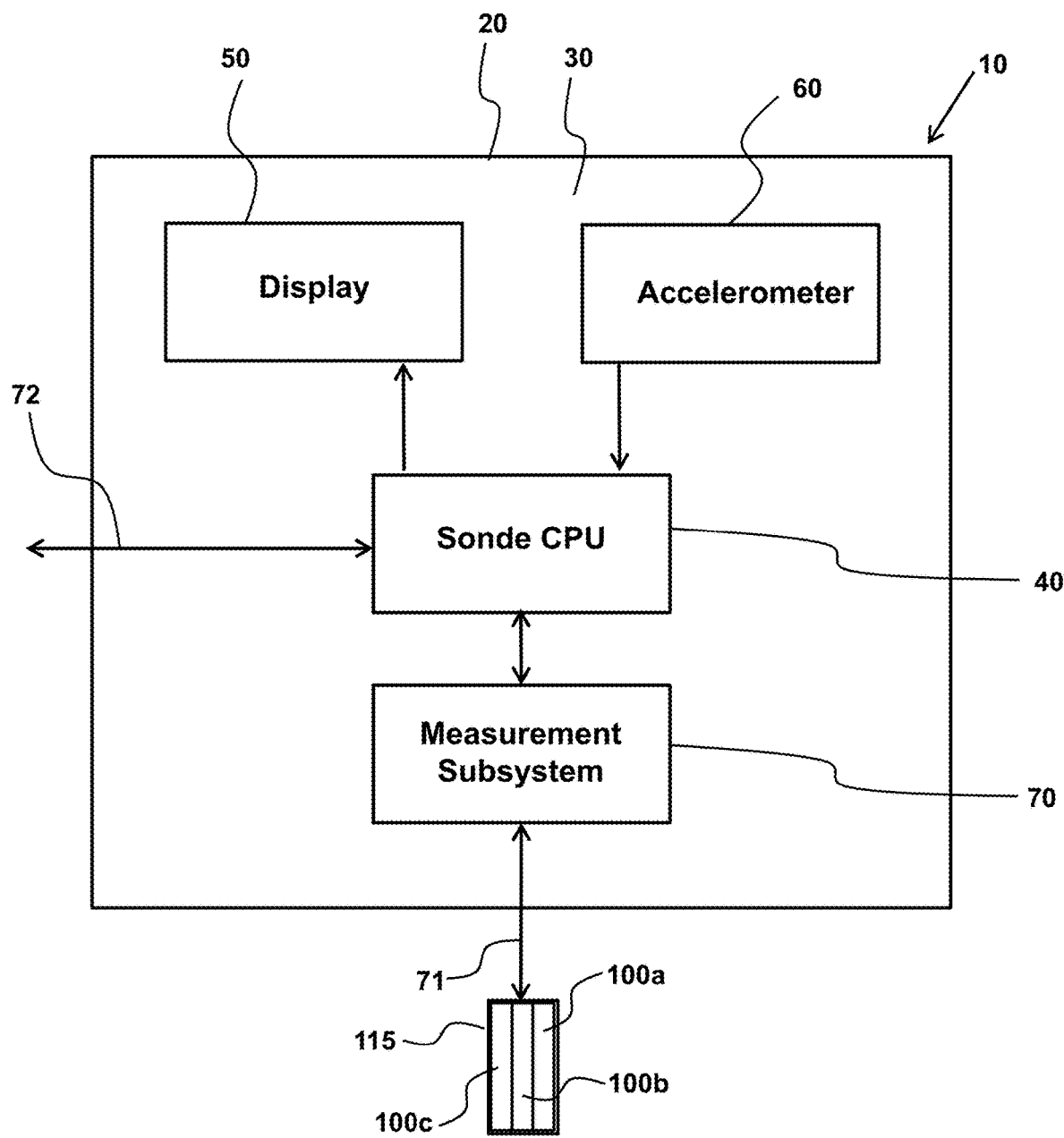
FIG. 1 is a block diagram illustrating the water-tight housing and the various components positioned therein that are associated with the integrated user-interface, including with communication and control of the user-interface.

In general, the terms and phrases used herein have their art-recognized meaning, which can be found by reference to standard texts, journal references and contexts known to those skilled in the art. The following definitions are provided to clarify their specific use in the context of the invention.

"Sonde" refers to a water quality monitoring instrument. "Multi-parameter" refers to a sonde having multiple independent separate sensors for providing multiple water parameter values.

"Independent sensors" refers to the ability to insert or remove a sensor without affecting other sensors. For example, one of the sensors may be removed and replaced with a sensor blank. Similarly, a user in the field may simply remove one independent sensor and replace it with another of the same or different sensor, without affecting the other sensors. "Sensor blank" refers to an equivalently shaped object that is used in place of a sensor. It is useful if the user does not need or have a sensor to connect to the base so as to fully fill the sensor guard.

The devices provided herein are compatible with a range of sensors, including sensors that measure conductivity, dissolved oxygen (DO), oxygen-reduction potential (OR), pH, pressure, depth, level, turbidity, ion selective electrodes for various ions, such as nitrate, ammonium and chloride, temperature.

"Accelerometer" refers to a device that can provide an output dependent on the device's orientation. For example, by measuring acceleration forces, the device can determine orientation. Examples include devices that have three orthogonally arranged one-axis accelerometers, each producing a signal corresponding to acceleration in an x-, y- or z-direction.

"Optically transparent" refers to a material through which a display output can be observed. Accordingly, the material need not be completely optically transparent, but may reflect, refract or absorb light, so long as sufficient light passes through the material that a user can observe and understand the display output. In an aspect, to assist with viewing in low-light conditions, the display may be illuminated, such as by back-light illumination.

Unless defined otherwise, "substantially" refers to a value that is within at least 20%, within at least 10%, or within at least 5% of a desired or true value. Substantially, accordingly, includes a value that matches a desired value.

"Operably connected" refers to a configuration of elements, wherein an action or reaction of one element affects another element, but in a manner that preserves each element's functionality. For example, a plurality of sonde sensors operably connected to a display refers to the ability of the display to provide an output display configuration without impacting the functionality of the sensors. "Releasably connected" or "releasably connects" refers to a configuration of elements, wherein the elements can be temporarily connected to each other and, as desired, removed from each other without adversely impacting the functionality of other elements of the device. "Electrically" or "electronically connected" refers to a configuration of elements, where an electric or electronic output from one element is communicated to another element, without adversely impacting the functionality of other elements of the device.

"Measurement subsystem" refers to those conventional electronics associated with sondes known in the art, such as standard electrical circuits that provide power, communicate with sensors, and the like. The electrical circuits may be in the form of printed circuit boards, chips, processors, with associated resistors, capacitors, switches, diodes, transistors and other basic electronic components to achieve the desired circuit, power and communication connections and functionality.

Example 1: Integrated User Interface

Referring to FIG. 1, the integrated user interface 10, comprises a water-tight housing 20 that forms a water-tight volume 30. Within the water-tight volume, a sonde CPU 40, a display 50, accelerometer 60 and measurement subsystem 70 are positioned. The arrows in FIG. 1 indicate electronic interconnections. The measurement subsystem includes various conventional electronic circuitry for connecting the sonde CPU with a plurality of independent sensors, illustrated as 100a 100b and 100c. The invention is compatible with any number of sensors and is particularly suited for multiple sensors, where it is otherwise difficult to achieve control and understanding of the sonde without an external device connected to the sonde, such as through external connection port 72. The sensors are electronically connected to the sonde CPU via the measurement subsystem through electronic connection 71, which is watertight to ensure no water leakage into water-tight volume 30

Example 2: Incorporation into a Submersible Multi-Parameter Sonde

Figure 2:
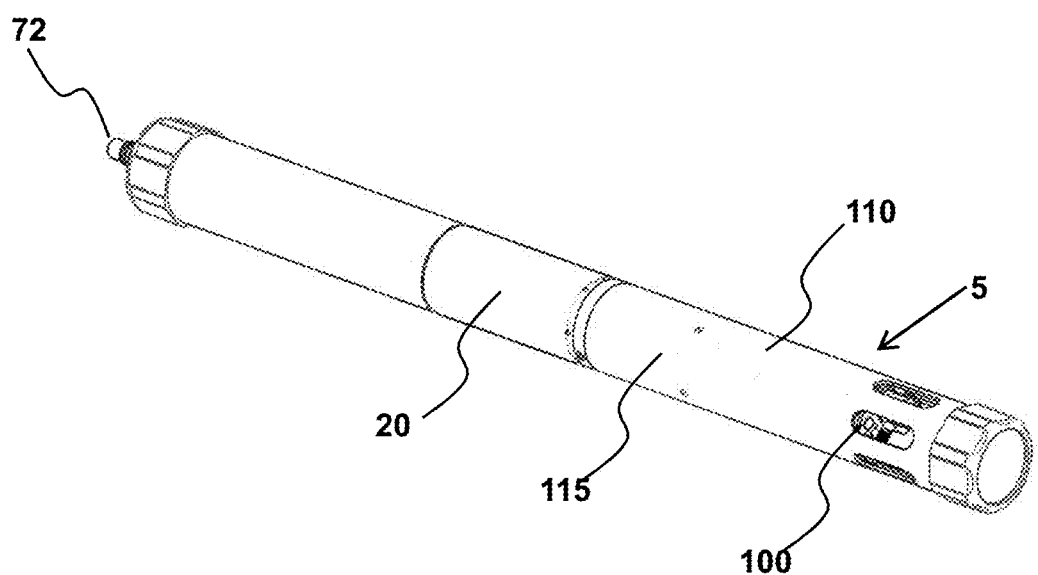
FIG. 2 is a schematic illustration of a multi-parameter sonde to illustrate the integration of the water-tight housing of FIG. 1 with the rest of the sonde, including with the sensors.

Referring to FIG. 2, and also U.S. Provisional Pat. App. No. 62/077,528 titled "Submersible multi-parameter sonde having a high sensor form factor sensor" by Scott et al., filed Nov. 10, 2014 and specifically incorporated by reference for the sondes disclosed therein, any of the integrated user interfaces may be integrated into a sonde. One example of such a sonde 5 is provided in FIG. 2. Sonde sensors 100 are positioned in sensor housing 110, such as a sensor guard 115. The sensors and housing, are then operably connected, such as to establish the electronic connection 71 illustrated in FIG. 1. The resultant sonde, then has a nicely integrated user interface 20 portion within the sonde as a whole.

Figure 3:
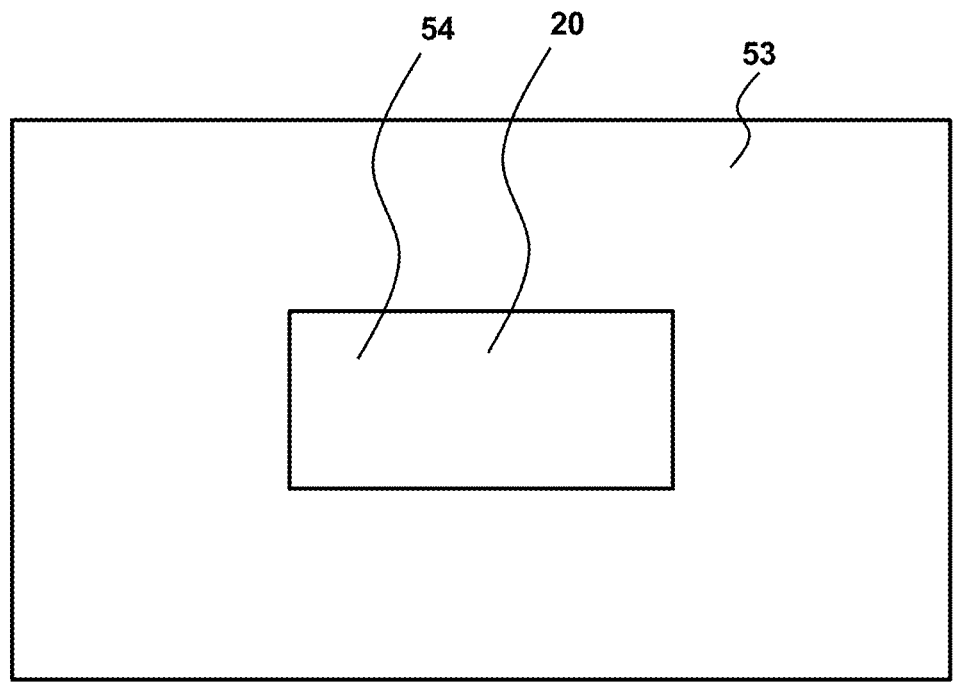
FIG. 3 illustrates use of a sleeve around the water-tight housing that assists with framing the display for viewing by a user. The top panel is a side view and the bottom panel an end view, looking down a longitudinal direction of the water-tight housing that is cylindrically shaped.
Figure 3:
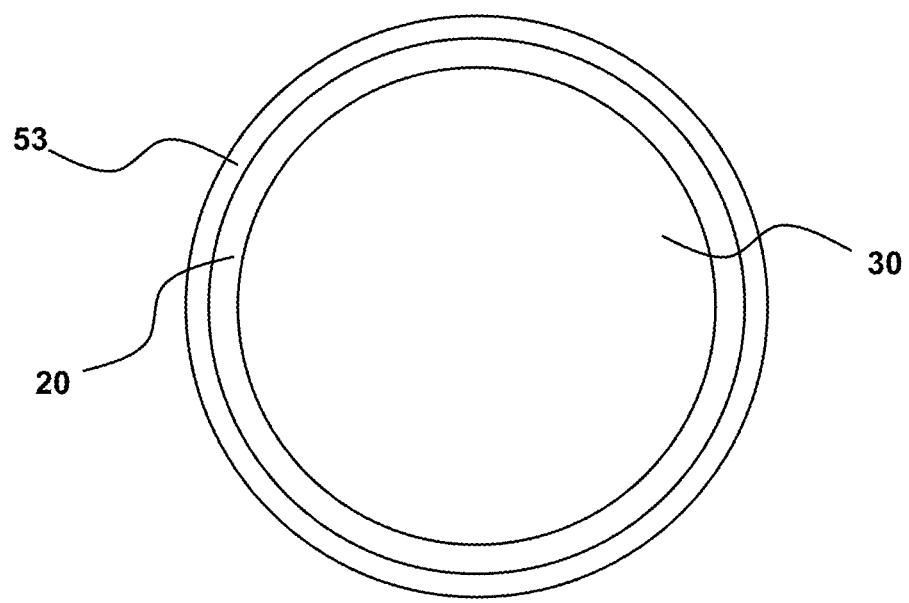

The actual display 50, which is the portion of interest to the user, is located within watertight housing 20. To increase user convenience, the display position may be emphasized by making only that portion of 20 that optically corresponds to the display transparent. The other regions may be optically masked or colored. One option for achieving this is illustrated in FIG. 3 by use of a sleeve 53 over the optically transparent and watertight housing 20. The top panel is a side-view illustrating sleeve 53 and viewing window 54 over that portion of the watertight housing 20 that optically aligns with an underlying display. The bottom panel of FIG. 3 is an axial view of the top panel, showing the sleeve 53 covering the watertight housing 20 and the watertight internal volume 30.

Figure 4:
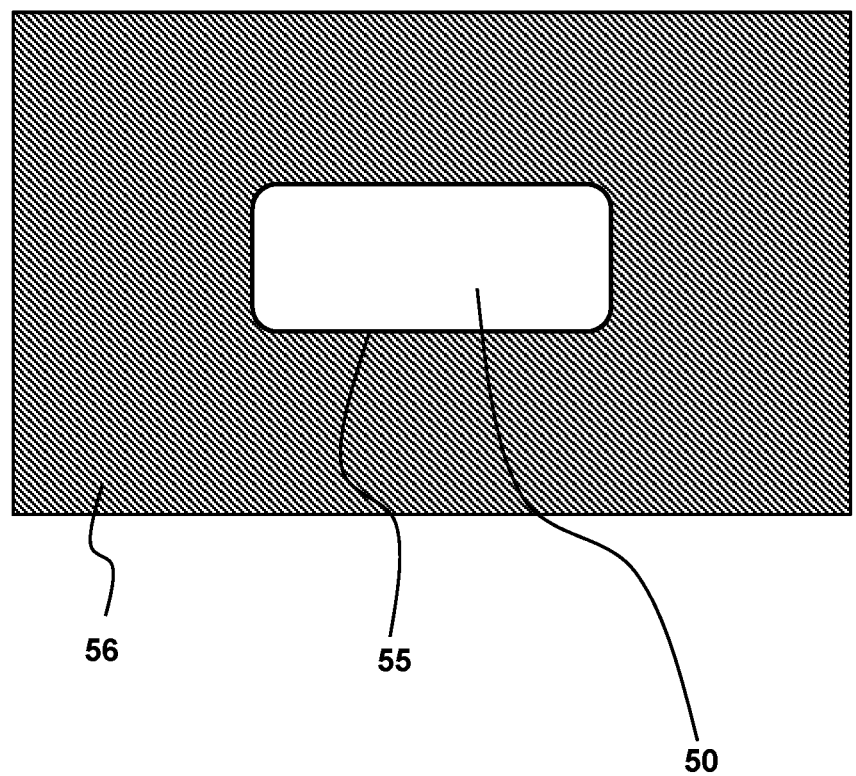
FIG. 4 illustrates an alternative means for framing the display without use of a separate physical component, such as a sleeve of FIG. 3.
Figure 5:
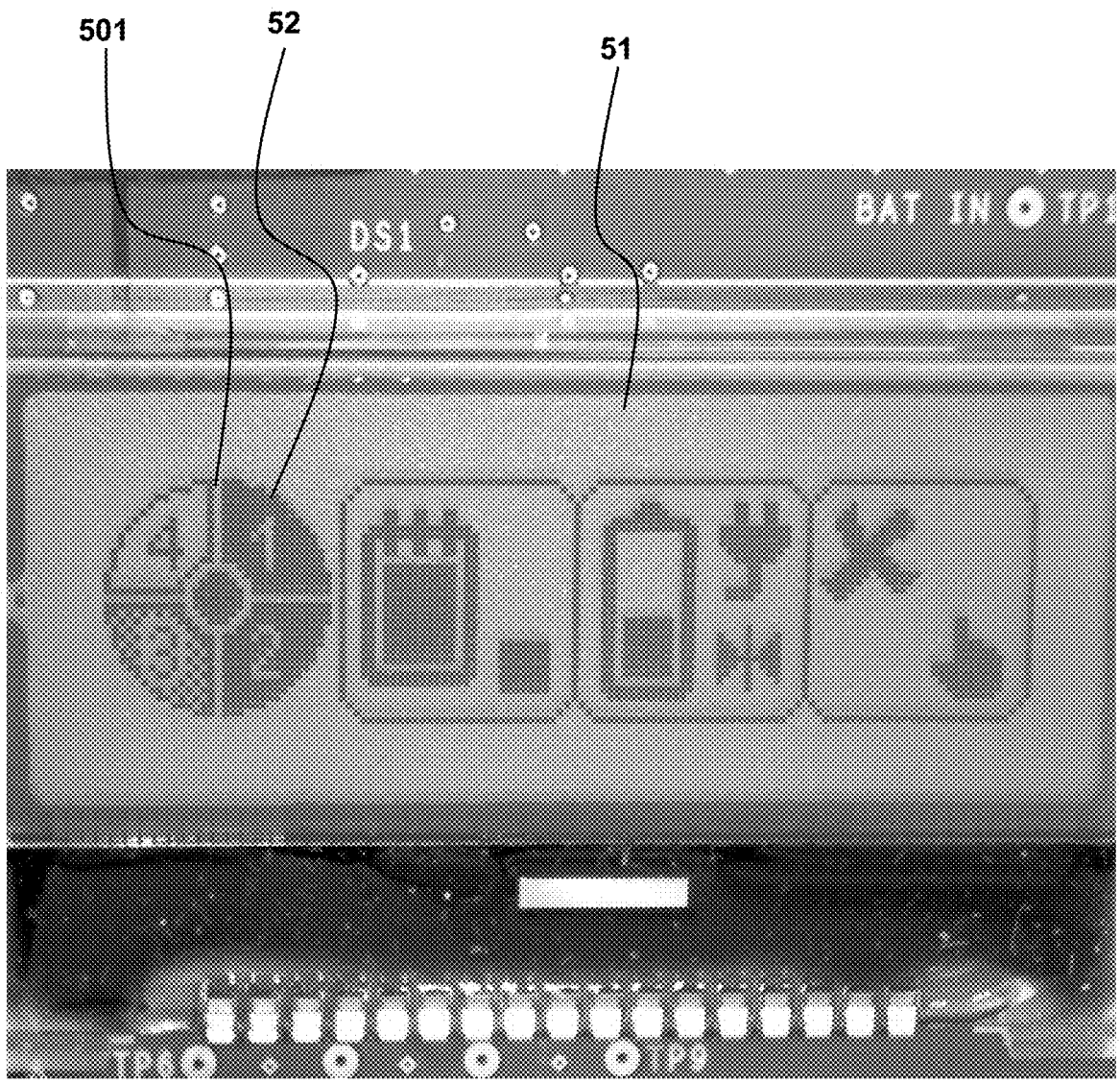
FIG. 5 is a screen-shot capture of the display in a home screen mode.

Optionally, instead of leaving the water-tight housing in a completely transparent configuration to a user, the regions of the housing that are not optically aligned with the display for user viewing may be masked. This is referred herein as a viewing window. FIG. 4 illustrates a side view of the watertight housing having an optically transparent portion or viewing window 55 with an underlying display 50, and a non-optically transparent portion 56. In this manner, the user's eye is quickly drawn to the display, thereby facilitating the direction of a user's attention to the region of interest instead of having to examine the entire outer surface of the sonde to find the display.

Example 3: User Control and Navigation

FIGS. 5-8 are screen capture shots of the display to illustrate user control of the sonde by the integrated user interface of the instant invention, including examples of various output display configuration and display value. The output information in the display is generally referred herein as output display configuration 51. The round image 501 represents status of plug-in sensors. In this manner, a display value 52 that indicates the presence or absence of a connected sensor is displayed to a user. A dark image indicates that a sensor is plugged into the port, a gray (dithered) image indicates that a port plug or blank is plugged in, a white image indicates that the port is not properly plugged.

From the left, the first box is the data log status. The notepad indicates how much data capacity is available. The block indicates the log is stopped (not running). The block changes to a "play" arrow if the data log is running (the sonde is actively recording data).

The second box is the power status. The example shows that the battery capacity is down to 40%, external power is connected to the sonde, and that the battery compartment is open and needs to be closed.

The third box is overall sonde status and navigation guide. The "X" indicates that the sonde is not ready to deploy (port 4 is open, the log is not running, the battery compartment is open). The hand image indicates that the sonde can be double-tapped to obtain more functionality. These are all non-limiting examples of display values within a specific output display configuration that communicate to the user various sonde status data. Accordingly, in one aspect the output display configuration is a plurality of display values having graphical representations, including port status, data logging status, data capacity, battery capacity, external power connection, battery compartment status, sonde readiness status and any combination thereof.

Figure 6:
FIG. 6 is a screen-shot capture of the display showing the main menu, such as from a double-tapping force for the sonde of FIG. 5.

When the sonde is double-tapped from the status or home screen display, the sonde display presents a main menu (FIG. 6). The arrows in the navigation guide indicate that the sonde may be tilted down to the left or right to move up or down in the menu respectively. A gray arrow indicates that the user is at the top or bottom of the menu with no more options in that direction. The hand indicates that a double-tap will select the highlighted menu option.

Figure 7:
FIG. 7 is a screen-shot capture of the display illustrating navigation of the main menu by tilting or tapping the sonde, including by tilting the sonde of FIG. 6.

FIG. 7 shows the output display configuration after the user has tilted the sonde to the right and gone down one item in the main menu of FIG. 6, highlighting the "Contrast" option. The display correspondingly changes to indicate that the sonde may now be tilted in either direction to scroll through the menu. The user double-taps the sonde to select the contrast option (see, e.g., FIG. 8).

Figure 8:
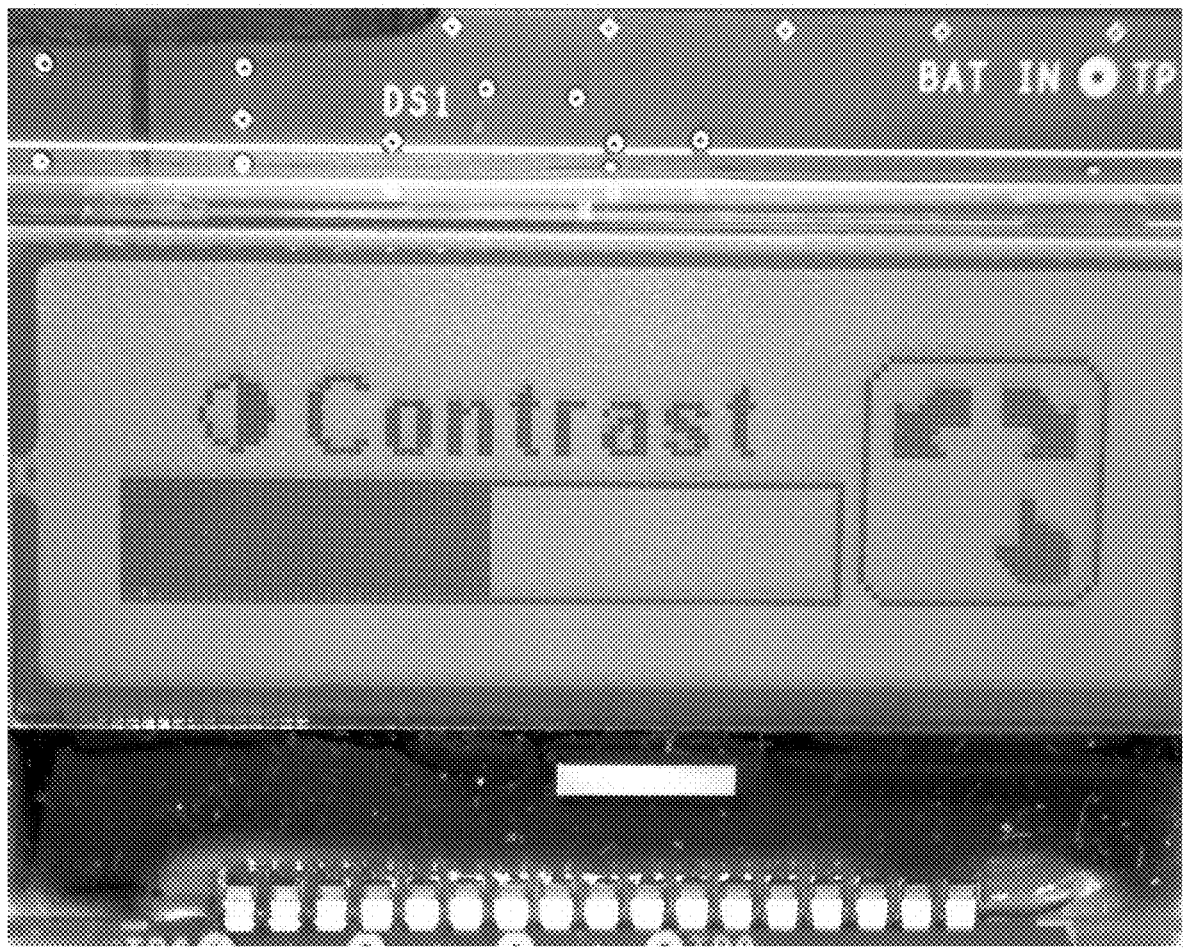
FIG. 8 is a screen-shot capture of the display illustrating selection of a parameter and how a value associated with that parameter can be controlled. In this illustration the parameter is display contrast that was selected by double tapping the sonde of FIG. 7, whose value is adjusted up by tilting in one direction and down by tilting in another direction.

After double-tapping the sonde with the contrast option highlighted in FIG. 7, the sonde presents the contrast adjustment screen, as illustrated in FIG. 8. The user tilts the sonde down to the left or right to lighten or darken the display respectively. The user double-taps the sonde to select the new contrast and the display returns to the home status display.

Other sonde features are selected in a similar manner: wake the sonde to obtain the home status display, double-tap the sonde to enter the main menu, tilt the sonde to highlight an available feature, double-tap the sonde to select the feature. In this manner, sonde functionality may be controlled and status monitored by a user in the field without the need for any external electronics.

Example 4: Method of Using the Integrated User Interface

Figure 9:
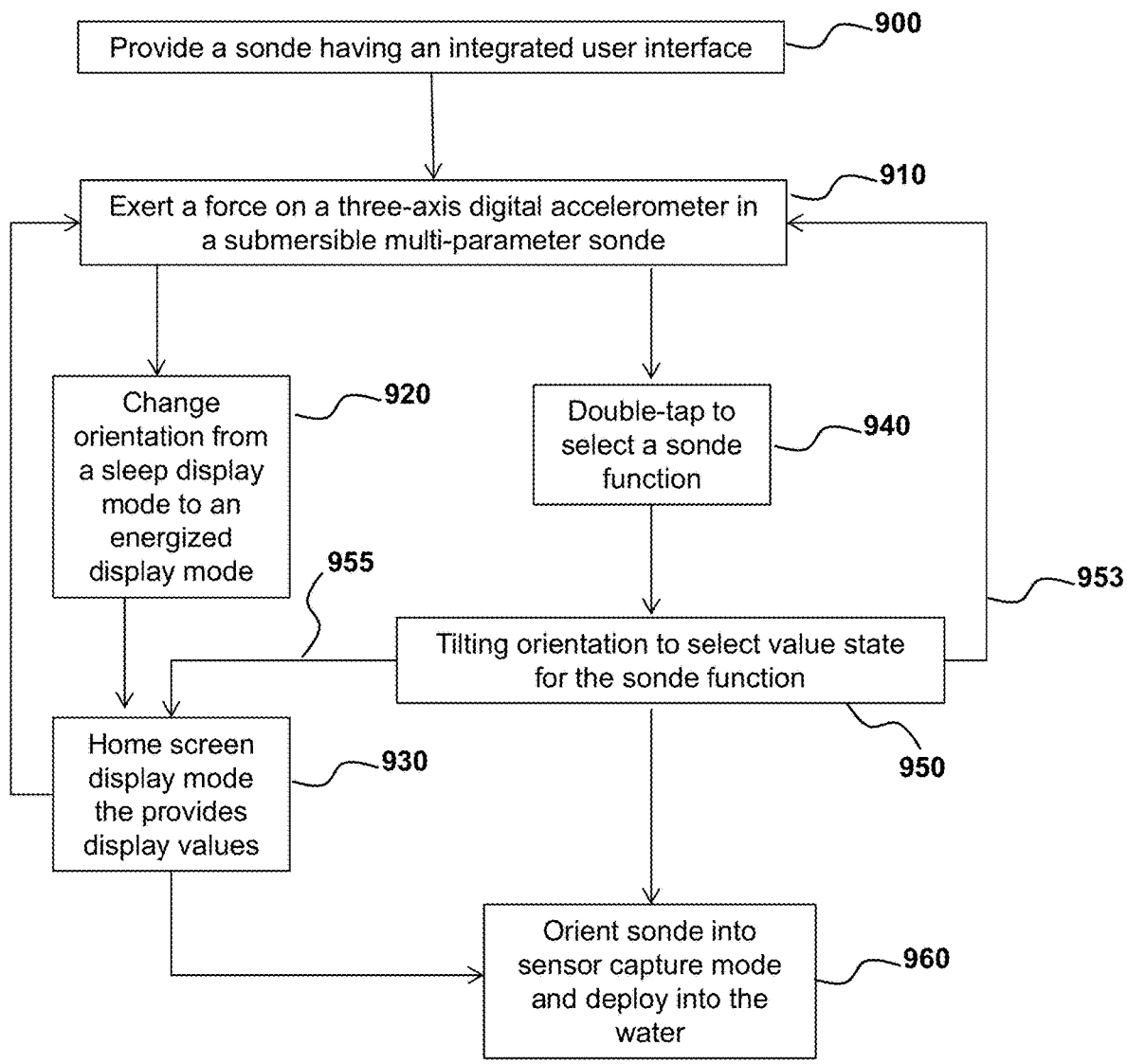
FIG. 9 is a flow chart summary illustrating a method of using the integrated user display for sonde status assessment and control.

FIG. 9 is a flow-chart summary of one method of the instant invention. Briefly, the sonde is provided in step 900 and is ready to receive an exerted force, including for any of the sondes described in U.S. Pat. App. No. 62/077,528. The accelerometer senses forces that may be rotation direction (tilting, including left/right tilt) or an impulse force (tapping or double tapping) 910. Upon appropriately orienting the sonde, such as by a change in orientation 920 a home screen output display configuration is generated 930. As desired, after checking that the display values in the home screen are appropriate for sonde deployment, the sonde may be oriented and deployed by submersion into the water 960, where the display may enter into a sleep mode to minimize energy use. Alternatively, additional action may be taken, as reflected by a return arrow to step 910 and a double tap from the home screen 940. This provides user control of various sonde functions, with control that may be achieved by tilting in one direction to increase a value and tilting in another direction to decrease a value. As desired, other sonde functions may be changed as indicated by return arrows 953 955. When the desired sonde function is attained, the sonde may be deployed in step 960.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure.

Every combination of elements described or exemplified herein can be used to practice the invention, unless otherwise stated.

Whenever a range is given in the specification, for example, a size range, an angle range, or a time or a number range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that materials and methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

I claim:

1. A method for displaying status and diagnostic information of a submersible multi-parameter sonde on an outer-facing surface of the submersible multi-parameter sonde, the method comprising the steps of:
    exerting a force on a three-axis digital accelerometer in a submersible multi-parameter sonde;
    outputting to a processor a signal from said three-axis digital accelerometer based on said exerted force;
    processing said signal with said processor to determine a force parameter; and
    generating with a display an output display on the outer-facing surface of the submersible multi-parameter sonde based on said force parameter;
    wherein said accelerometer, said processor and said display are contained in a water-tight housing and said output display provides sonde status, diagnostic information, sonde status, diagnostic information, or any combination thereof;
    thereby displaying status and diagnostic information of the submersible multi-parameter sonde on the outer facing surface of the submersible multi-parameter sonde.

2. The method of claim 1, wherein said exerted force comprises:
    tapping or double tapping said submersible multi-parameter sonde; or
    changing an orientation of said submersible multi-parameter sonde between an upward and downward facing directions.

3. The method of claim 2, wherein said changing the orientation step changes a state of said sonde from a sleep mode to an active mode that provides said output display.

4. The method of claim 2, wherein said tapping provides user-control over a sonde function.

5. The method of claim 4, wherein:
    said output display comprises one or more of:
        sonde deployment readiness;
        watertight status of an accessory port;
        operational status of all data logging functions;
        battery condition;
        external power connection; or
        readings from connected sensors;
    said sonde function comprises user control of one or more of:
        operation mode;
        data log configuration;
        starting and stopping of data logs; or
        sensor calibration.

6. The method of claim 1, wherein said output display is provided without external connection to a controller or a display.

7. The method of claim 6, further comprising the step of:
    configuring modes of operation;
    configuring data logs;
    starting and stopping data logs;
    calibrating sensors, and
    controlling the output display.

8. The method of claim 1, wherein the submersible multi-parameter sonde comprises: a plurality of sonde sensors operably connected to the display.

9. The method of claim 1, wherein said water-tight housing is formed from a unitary material that is optically transparent.

10. The method of claim 1, wherein said unitary material comprises a clear plastic housing that is cylindrically shaped.

11. The method of claim 1, wherein said water-tight housing comprises an optically transparent portion and a non-optically transparent portion, said optically transparent portion aligned with said display and configured to allow a user to view said display through said water-tight housing.

12. The method of claim 1, wherein said display comprises a liquid crystal display having a back light.

13. The method of claim 1, wherein said water-tight housing is water-tight to a maximum depth that is greater than or equal to 600 feet.

14. The method of claim 1, wherein said output display comprises a plurality of display values having graphical representations, selected from the group consisting of: port status of all available ports, data logging status, data capacity, battery capacity, external power connection, battery compartment status, sonde readiness status and any combination thereof.

* * * * *